(12) United States Patent
Gilkerson et al.

(10) Patent No.: US 6,381,494 B1
(45) Date of Patent: Apr. 30, 2002

(54) RESPONSE TO AMBIENT NOISE IN IMPLANTABLE PULSE GENERATOR

(75) Inventors: James O. Gilkerson, Stillwater; David L. Perschbacher, Coon Rapids; Doug M. Birkholz; Thomas J. Harris, both of Shoreview, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/378,321

(22) Filed: Aug. 20, 1999

(51) Int. Cl.$^7$ .............................. A61N 1/36
(52) U.S. Cl. ............................ 607/27; 607/9
(58) Field of Search .................. 607/9, 17, 18, 607/25, 27

(56) References Cited

U.S. PATENT DOCUMENTS

| | | | |
|---|---|---|---|
| 4,527,567 A | 7/1985 | Fischler et al. | 128/419 |
| 4,550,370 A | 10/1985 | Baker | 364/413 |
| 4,558,702 A | 12/1985 | Barreras et al. | 128/419 |
| 4,674,508 A | 6/1987 | DeCote | 128/419 |
| 4,674,509 A | 6/1987 | DeCote | 128/419 |

(List continued on next page.)

FOREIGN PATENT DOCUMENTS

| | | | |
|---|---|---|---|
| EP | 0707866 | 9/1995 | A61N/1/365 |
| WO | 0707866 A2 * | 4/1996 | A61N/1/365 |

*Primary Examiner*—Carl Layno
(74) *Attorney, Agent, or Firm*—Schwegman, Lundberg, Woessner & Kluth, P.A.

(57) ABSTRACT

A method and system for response to ambient noise in implantable pulse generator. At least one cardiac signal is sensed with an implantable pulse generator. Cardiac depolarizations are identified in the at least one cardiac signal and cardiac depolarization markers are generated. The at least one cardiac signals are then analyzed for a noise event during a refractory period following the detected cardiac depolarization. The refractory period includes a noise window interval during which noise events are recognized. When a noise event, or events, occur during the noise window interval a first noise marker is generated. The noise window interval is then repeated as long as noise is detected in the noise window intervals. When the noise persists for a predetermined time interval a second noise marker is generated.

21 Claims, 4 Drawing Sheets

U.S. PATENT DOCUMENTS

| | | | |
|---|---|---|---|
| 4,677,986 A | | 7/1987 | DeCote, Jr. ................. 128/697 |
| 4,721,114 A | | 1/1988 | DuFault et al. ............. 128/696 |
| 4,779,617 A | * | 10/1988 | Whigham ............... 128/419 P |
| 4,819,643 A | | 4/1989 | Menken ...................... 128/419 |
| 5,010,888 A | | 4/1991 | Jadvar et al. ............... 128/696 |
| 5,127,401 A | | 7/1992 | Grevious et al. ........... 128/419 |
| 5,184,615 A | | 2/1993 | Nappholz et al. ........... 128/419 |
| 5,231,987 A | | 8/1993 | Robson ....................... 607/29 |
| 5,233,983 A | | 8/1993 | Markowitz ................... 607/42 |
| 5,233,986 A | | 8/1993 | Robson ......................... 607/4 |
| 5,251,622 A | | 10/1993 | Robson ....................... 607/19 |
| 5,265,603 A | | 11/1993 | Hudrlik ........................ 607/9 |
| 5,265,617 A | | 11/1993 | Verrier et al. ............... 128/704 |
| 5,289,824 A | | 3/1994 | Mills et al. ................. 128/696 |
| 5,300,093 A | | 4/1994 | Koestner et al. .............. 607/32 |
| 5,312,445 A | | 5/1994 | Nappholz et al. .............. 607/9 |
| 5,317,269 A | | 5/1994 | Mills et al. ................. 324/427 |
| 5,333,616 A | | 8/1994 | Mills et al. ................. 128/696 |
| 5,336,244 A | | 8/1994 | Weijand ...................... 607/21 |
| 5,342,406 A | | 8/1994 | Thompson .................. 607/22 |
| 5,351,695 A | | 10/1994 | Mills et al. ................. 128/696 |
| 5,372,135 A | | 12/1994 | Mendelson et al. ......... 128/633 |
| 5,379,775 A | | 1/1995 | Kruse ......................... 128/697 |
| 5,391,192 A | | 2/1995 | Lu et al. ...................... 607/28 |
| 5,425,373 A | | 6/1995 | Causey, III ................ 128/697 |
| 5,435,316 A | | 7/1995 | Kruse ......................... 128/697 |
| 5,437,285 A | | 8/1995 | Verrier et al. ............... 128/702 |
| 5,448,997 A | | 9/1995 | Kruse et al. ................. 128/697 |
| 5,527,347 A | | 6/1996 | Shelton et al. ................. 607/9 |
| 5,555,888 A | | 9/1996 | Brewer et al. .............. 128/702 |
| 5,560,370 A | | 10/1996 | Verrier et al. ............... 128/705 |
| 5,564,430 A | | 10/1996 | Jacobson et al. ........... 128/697 |
| 5,613,495 A | | 3/1997 | Mills et al. .................. 128/696 |
| 5,620,472 A | | 4/1997 | Rahbari ....................... 607/27 |
| 5,626,621 A | | 5/1997 | Skoglund et al. ............. 607/10 |
| 5,658,320 A | * | 8/1997 | Betzold et al. ............... 607/14 |
| 5,683,432 A | * | 11/1997 | Goedeke et al. ............. 607/32 |
| 5,694,943 A | * | 12/1997 | Brewer et al. .............. 128/702 |
| 5,709,213 A | * | 1/1998 | Kruse et al. ................. 128/696 |
| 5,766,227 A | | 6/1998 | Nappholz et al. .............. 607/9 |
| 5,766,232 A | * | 6/1998 | Grevious et al. ............. 607/60 |
| 5,813,991 A | * | 9/1998 | Willis et al. ................. 600/510 |
| 5,817,135 A | * | 10/1998 | Cooper et al. ................ 607/17 |
| 5,836,989 A | * | 11/1998 | Shelton ....................... 607/27 |
| 5,842,997 A | * | 12/1998 | Verrier et al. ............... 600/518 |
| 5,843,139 A | * | 12/1998 | Goedeke et al. ............. 607/32 |
| 5,861,013 A | * | 1/1999 | Peck et al. .................... 607/28 |
| 5,871,512 A | * | 2/1999 | Hemming et al. ............ 607/28 |
| 5,873,898 A | * | 2/1999 | Hemming et al. ............ 607/28 |
| 5,899,928 A | * | 5/1999 | Sholder et al. ............... 607/27 |
| 5,921,940 A | * | 7/1999 | Verrier et al. ............... 600/518 |
| 5,954,661 A | * | 9/1999 | Greenspon et al. ......... 600/510 |
| 5,954,666 A | * | 9/1999 | Snell ........................... 600/523 |
| 5,954,756 A | * | 9/1999 | Hemming et al. ............ 607/28 |

* cited by examiner

RESPONSE TO AMBIENT NOISE IN IMPLANTABLE PULSE GENERATOR

FIELD OF THE INVENTION

This invention relates generally to the field of medical devices, and more particularly to a system and method which includes an implantable pulse generator.

BACKGROUND

Implantable pulse generators have been successfully used to treat patients having a variety of cardiac condition. For example, cardioverter/defibrillators (ICDs) have been successfully used to treat patients who have experienced one or more documented episodes of hemodynamically significant ventricular tachycardia or ventricular fibrillation. Implantable cardiac pacemakers have been successfully used to treat patients having a variety of cardiac rhythm management problems, including slow heart rates (symptomatic bradycardia) and in cases where the patient's AV node is irreversibly disabled.

The basic implantable pulse generator consists of a primary battery, electronic circuitry to control both the sensing of the patient's cardiac signals and the delivery of electrical shocks to the patient's heart, and one or more capacitors housed within a hermetically sealed titanium case. One or more catheter leads having electrodes are implanted within the heart of the patient or on the epicardial surface of the patient's heart. The catheter leads are then coupled to the implantable housing and the electronic circuitry of the implantable pulse generator and are used to deliver electrical energy to the heart.

The cardiac lead of the implantable pulse generator are used to sense cardiac complexes in and around the heart of the patient. Cardiac complexes generate a very weak current that must be amplified prior to being analyzed by the electronic circuitry of the implantable pulse generator. In addition to cardiac complexes, however, many signals unrelated to the cardiac complex, such as current due to pectoral muscle activity or external electromagnetic interference, cause additional weak currents in the implantable pulse generator system. These extraneous currents can be amplified and analyzed the by the electronic circuitry of the implantable pulse generator. When this happens there is the possibility that the extraneous signals could cause the implantable pulse generator to either inhibit necessary therapy or initiate inappropriate therapy to the patient.

To reduce the possibility that these currents will be inappropriately sensed as cardiac complexes, additional components are added to the sensing circuit. One is a level detector to prevent low-level electrical noise from being sensed. The other is a bandpass filter to help eliminate stronger signals that are of a different frequency than those associated with the cardiac complexes. While these additional components are helpful in reducing or eliminating some types of noise there exists noise signals sufficiently strong to overcome these components. For example, electromagnetic interference from certain types of machinery and equipment can be sufficient to create noise in an implantable pulse generator. When this happens noise is detected by the implantable pulse generator.

Implantable pulse generators interact with medical device programmers to transfer data and operating instructions between the two devices. The typical programmer is a microprocessor-based unit that has a wand for creating the telemetric link between the implanted pulse generator and the programmer, and a graphics display screen that presents a patient's recorded cardiac data and implantable pulse generator system information to the physician.

Typically, the physician will use the medical device programmer in a clinical setting where electromagnetic interference can be especially prevalent. During these clinical settings the operation (or the function) of the implantable pulse generator is tested with the medical device programmer. If an electromagnetic field is effecting the performance of the implantable pulse generator during this time, parameter settings for the implantable pulse generator my be incorrectly set due to the influence of the electromagnetic field. This could lead to a potentially dangerous situation for the patient.

For the reasons stated above, and for other reasons stated below which will become apparent to those skilled in the art upon reading and understanding the present specification, there is a need in the art for a system which is capable of signaling to a user the existence of noise presently being detected by an implantable pulse generator.

SUMMARY OF THE INVENTION

As explained in detail below, the present subject matter is directed to a system and method for the analysis and detection of noise in one or more cardiac signals sensed by an implantable pulse generator. As noise is detected in the one or more cardiac signals markers indicating the present of the noise are displayed to a user interacting with the implantable pulse generator. Thus, the present subject matter provides an advantage by providing information to an operator of the medical device programmer that noise is present on the sensing channels of the device and exactly what therapies are being delivered, or suppressed, because of the noise.

In one embodiment, at least one cardiac signal is sensed with an implantable pulse generator. Cardiac depolarizations are identified in the at least one cardiac signal and cardiac depolarization markers are generated. The at least one cardiac signals are then analyzed for a noise event during a refractory period following the detected cardiac depolarization. The refractory period includes a noise window interval during which noise events are recognized. When a noise event, or events, occur during the noise window interval a first noise marker is generated. The noise window interval is then repeated as long as noise is detected in the noise window intervals. When the noise persists for a predetermined time interval a second noise marker is generated.

A communication link is established between the implantable pulse generator and a medical device programmer. The at least one cardiac signal is transmitted from the implantable pulse generator to the medical device programmer. As the at least one cardiac signal is received, the medical device programmer displays the signal(s) on a display screen. In addition to displaying the cardiac signal(s), the medical device programmer also displays the cardiac depolarization marker, the first noise marker and the second noise marker on the display screen. In one embodiment, the markers are associated with the approximate location of where the event giving rise to the marker occurred. Additionally, the cardiac signal(s) and the markers may also be printed on paper.

These and other features and advantages of the invention will become apparent from the following description of the preferred embodiments of the invention.

DETAILED DESCRIPTION

Figure 1:
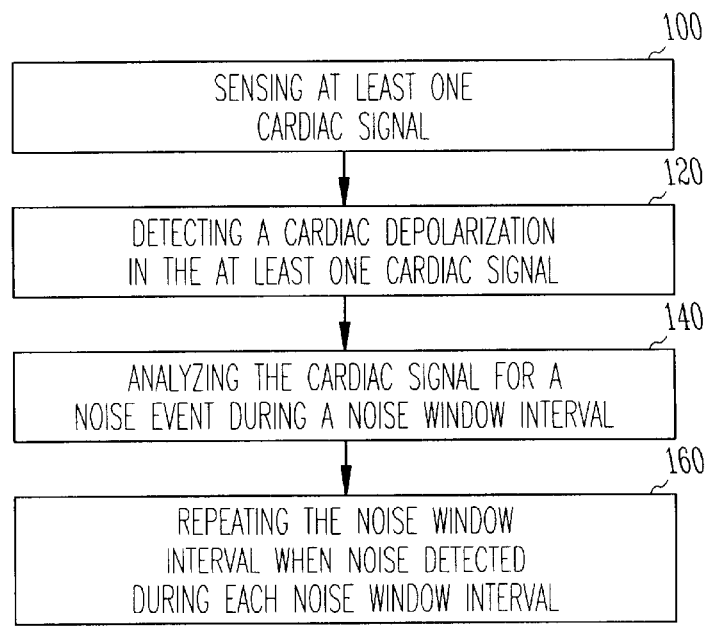
FIG. 1 is a flow chart illustrating one embodiment of the present subject matter.

In the following detailed description, references are made to the accompanying drawings that illustrate specific embodiments in which the invention may be practiced. Electrical, mechanical, programmatic and structural changes may be made to the embodiments without departing from the spirit and scope of the present invention. The following detailed description is, therefore, not to be taken in a limiting sense and the scope of the present invention is defined by the appended claims and their equivalents.

The embodiments of the present subject matter illustrated herein are described as being included in an implantable pulse generator. In one embodiment, the implantable pulse generator is an implantable cardioverter defibrillator, which may include numerous pacing modes known in the art. Alternatively, it is also possible to implement the present subject matter in an implantable cardiac pacemaker. Furthermore, although the present invention is described in conjunction with an implantable pulse generator having a microprocessor based architecture, it will be understood that the implantable pulse generator (or other implanted device) may be implemented in any logic based, custom integrated circuit architecture, if desired.

The present subject matter provides for analysis and detection of noise in one or more cardiac signals sensed by an implantable pulse generator. As noise is detected in the one or more cardiac signals markers indicating the present of the noise are displayed to a user interacting with the implantable pulse generator. Implantable pulse generators useful with the present subject matter include implantable cardioverter defibrillators and implantable cardiac pacemakers.

Detecting and identifying noise sensed by an implantable pulse generator is important in properly diagnosing and treating a patient. For example, noise protection circuits have been incorporated into implantable pulse generators in order to prevent noise signals from being detected as natural heart beats. When such false detection occurs, the pacing pulses are suppressed thus leading to a potentially dangerous situation for the patient. These noise protection circuits include filters to attenuate noise signals of particular frequencies and refractory periods during which time detected signals are ignored.

Implantable pulse generators that generate artificial stimulating pulses for the heart, and which may or may not be implanted in the body, are known. The pacing function of an implantable pulse generator can be classified into demand pacing and non-demand pacing. Demand pacing is a mode of operating an implantable pulse generator where the pulse generator senses electrical activity in the heart and provides pacing pulses only when the patient's heart activity falls below a specified rate. In non-demand pacing, artificial stimulating pulses are issued without regard to the presence or absence of a natural beat.

Implantable pulse generators that operate in demand mode are useful in providing therapy to treat bradycardia. Bradycardia is a cardiac condition associated with a heart rate that does not allow cardiac output to meet physiologic demands. Therapy for treating bradycardia includes providing cardiac pacing to an atrial location, a ventricular location, or both supraventricular and ventricular locations. Cardiac pacing allows the patient to maintain at least a minimum heart rate to meet their physiological demands. In one embodiment, the type of bradycardia pacing supplied include demand pacing. However, other pacing modes for providing bradycardia pacing are also known and useful in the context of the present subject matter.

In one embodiment, the noise sensed by the implantable pulse generator is the result of electromagnetic interference sensed by implantable electrodes and presented in one or more sensed cardiac channels. Examples of potential sources of electromagnetic interference include electromagnetic fields surrounding power lines, electric motors, light fixtures, medical devices (e.g., electrical cauterizing units), electrical thermal blankets, nuclear magnetic resonance machines, and other known electromagnetic fields.

Electromagnetic interference can be especially prevalent in a clinical setting, where there are more opportunities to encounter electromagnetic fields as compared to non-clinical settings. During these clinical settings the operation (or the function) of the implantable pulse generator is tested. If an electromagnetic field is effecting the performance of the implantable pulse generator during this time, parameter settings for the implantable pulse generator my be incorrectly set due to the influence of the electromagnetic field. Knowing when an electromagnetic field is effecting the operation of the implantable pulse generator is therefore important for properly programming the device.

In one embodiment, the present subject matter provides a response to noise sensed in an implantable pulse generator that is effective at providing bradycardia therapy. The analysis and response to the sensed noise is made by the implantable pulse generator. The display of the existence of the sensed noise is then made on a display screen of a medical device programmer that is in communication with the implantable pulse generator. In one embodiment, a sensed cardiac signal is displayed on the medical device programmer along with one or more markers (or symbols) that identify the existence of noise along the cardiac signal. In addition to displaying the markers, indicators are also provided on the medical device programmer screen to indicate the approximate time along the cardiac signal where the noise was detected.

Thus, the present subject matter is useful in identifying noise being created by a electromagnetic field in one or more cardiac signals supplied to a medical device programmer for viewing and analysis from an implantable pulse generator. Additionally, the present subject matter provides an advantage by providing information to an operator of the medical device programmer that noise is present on the sensing channels of the device and exactly what therapies are being delivered, or suppressed, because of the noise.

Referring now to FIG. 1, there is shown a flow chart of one embodiment of the present subject matter. At 100, at least one cardiac signal is sensed with an implantable pulse generator. In one embodiment, a ventricular cardiac signal is sensed across a ventricular region of a heart, where the ventricular cardiac signal is either a far-field signal or a near-field signal. In one embodiment, the far-field signal is sensed between at least two defibrillation electrodes and the near-field signal is sensed between a pacing electrode and a second electrode (e.g., a defibrillation electrode or a second pacing electrode). In an additional embodiment, a first cardiac signal is sensed across a ventricular region and a second cardiac signal is sensed across a atrial region. Combinations of near-field and far-field signals can be sensed for the first and second cardiac signals. For example, a far-field signal is sensed across the ventricular region and a near-field signal is sensed across the atrial region.

At 120, a cardiac depolarization is identified in the at least one cardiac signal. In one embodiment, the at least one cardiac signal is the ventricular cardiac signal and the identified cardiac depolarization is a detected R-wave or QRS-complex resulting from the sensed cardiac cycle. Alternatively, when the first and second cardiac signals are sensed, there is a first cardiac depolarization (e.g., complex) detected in the first cardiac signal and a second cardiac depolarization (e.g., complex) detected in the second cardiac signal. The first cardiac depolarization is either a detected R-wave or QRS-complex sensed across the ventricular region and the second cardiac depolarization is a detected P-wave sensed across an atrial region. Alternatively, identifying the occurrence of the cardiac depolarization includes producing a pacing level pulse, and identifying the cardiac depolarization when the pacing level pulse is produced.

At 140, the at least one cardiac signal is then analyzed after the detected cardiac depolarization for a noise event occurring during a refractory period. As previously discussed, the refractory period occurs after the detected cardiac complex and is an interval over which cardiac activity (e.g., changes in the cardiac signal) are ignored by the implantable pulse generator. By ignoring sensed signals after the cardiac complex (paced or unpaced) the implantable pulse generator does not sense either the T-wave of the preceding QRS-complex (in the case of sensed ventricular depolarizations) or the pacemaker after-potential (for both sensed ventricular and atrial depolarizations). However, the present subject matter includes a region in the refractory period where the analysis circuitry within the implantable pulse generator does analyze the sensed cardiac activity. The region is termed a noise window interval.

In one embodiment, the last forty (40) milliseconds of the refractory period is designated as the noise window interval. In one embodiment, the noise window interval is retriggerable or repeatable under certain predetermined conditions. In one embodiment, the predetermined condition required for the noise window interval to repeat is when a noise event is sensed in the cardiac signal. In one embodiment, the cardiac signal includes a voltage and analyzing the at least one cardiac signal for the noise event includes detecting when the voltage of the cardiac signal exceeds a predetermined sensing floor value. The predetermined sensing floor value is programmable in the range of 0.18 to 0.45 millivolts, where 0.27 millivolts is an acceptable value.

At 160, the noise window interval is repeated when a noise event occurs during each noise window interval. Thus, during the refractory period there is an initial noise window interval that when noise is detected in the initial noise window subsequent noise window intervals are triggered to occur as long as noise is sensed during the noise window interval. In other words, the noise window interval is repeated when a noise event is sensed in a noise window interval preceding the repeated noise window interval. This retriggering of the noise window interval occurs until noise is no longer sensed in the cardiac signal.

Figure 2:
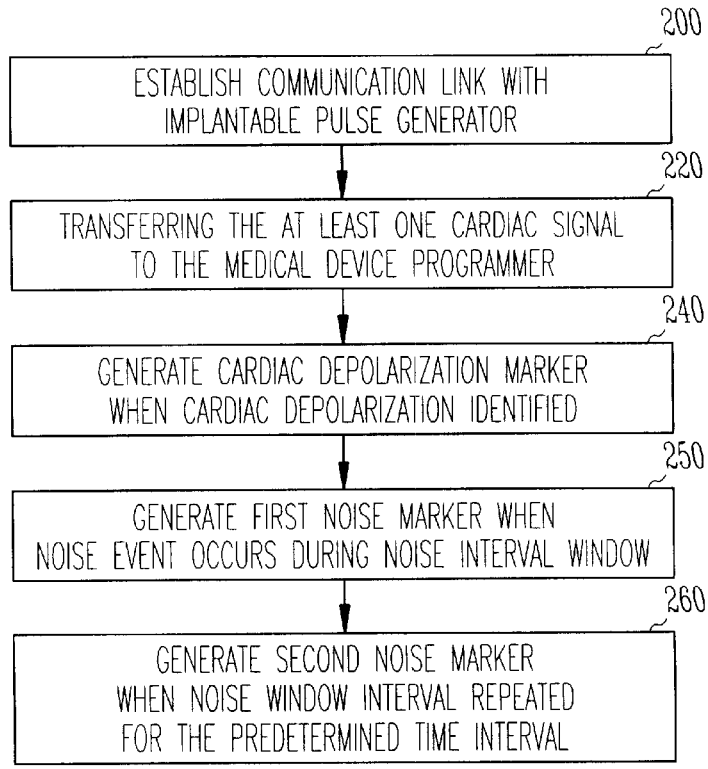
FIG. 2 is a flow chart illustrating one embodiment of the present subject matter.

Referring now to FIG. 2, there is shown an additional embodiment of the present subject matter. At 200, a communication link is established with the implantable pulse generator. In one embodiment, the communication link is established between the implantable pulse generator and a medical device programmer for the transmission of information between the two devices. For example, a radio frequency communication link is established between the implantable pulse generator and the medical device programmer that allows for cardiac data, information and programming instructions to be sent between the two devices.

At 220, the at least one cardiac signal sensed by the implantable pulse generator is transferred over the communication link to the medical device programmer. In one embodiment, the at least one cardiac signal is transferred in real time, where only a short delay exists between the time the cardiac signal is sensed and the time that it is transmitted to the medical device programmer. As the medical device programmer receives the one or more cardiac signals a plot, or tracing, of the voltage of the one or more cardiac signals versus the time is made. Included with the one or more cardiac signal are the cardiac depolarizations detected in the one or more cardiac signals, where the plot of the one or more cardiac signals include at least one cardiac depolarization. In one embodiment, the plot is generated on a display screen integrated into the medical device programmer. Alternatively, the plot is printed on paper from a chart recorded coupled to, or integrated into, the medical device programmer.

At 240, a cardiac depolarization marker is generated by the implantable pulse generator when the cardiac depolarization is identified. The cardiac depolarization marker is then transmitted to the medical device programmer through the communication link. The cardiac depolarization marker is then displayed on the display screen. In one embodiment, the cardiac depolarization marker is positioned adjacent and/or below to the cardiac depolarization in the at least one cardiac signal so as to associate the cardiac depolarization marker and the sensed cardiac depolarization.

At 250, a first noise marker is generated when the noise event occurs during the noise interval window. The first noise marker is then transmitted to the medical device programmer through the communication link. The first noise marker is then displayed on the display screen. In one embodiment, the first noise marker is positioned adjacent and/or below the approximate location along the cardiac signal where the noise event occurred so as to associate the first noise marker and the noise event. In one embodiment, the first noise marker and the approximate location where the noise event was detected are associated through the use of an arrow displayed on the display screen which links the noise event and the first noise marker.

As previously mentioned, the noise window interval is a repeatable, or retriggerable window. In one embodiment, this means that when a noise event is detected, or sensed, in one or more of the cardiac signals an additional noise window interval is started once the initial noise window interval ends in which the noise event was detected. This process then repeats itself for the additional noise window interval, where the implantable pulse generator analyzes the one or more cardiac signals during the additional noise window interval to detect the present of one or more noise events. When a noise event is detected in the additional noise window interval, another additional noise window interval is begun. Thus, as long as a noise event is detected in the noise window interval, the noise window interval will be repeated and monitored for noise events.

At 260, a second noise marker is generated when the noise window interval is repeated for the predetermined time interval. In other words, the second noise marker is generated when the total time of the repeated noise window intervals is equal to the predetermined time interval. In one embodiment, this indicates the presence of an electromagnetic field of sufficient strength to produce noise in the one or more sensing channels of the implantable pulse generator. If during a noise window interval, however, a noise event is not detected, returns to sensing the cardiac signal for cardiac depolarizations (i.e., returns to 120 of FIG. 1).

The second noise marker is transmitted to the medical device programmer through the communication link. The second noise marker is then displayed on the display screen at a position that is relative to the predetermined time interval. In one embodiment, the second noise marker is positioned adjacent and/or below the location of the predetermined time interval along the plot of the cardiac signal so as to associate the second noise marker and the predetermined time interval. In one embodiment, the second noise marker and the approximate location of the predetermined time interval are associated through the use of an arrow displayed on the display screen which links the two events.

Figure 3:
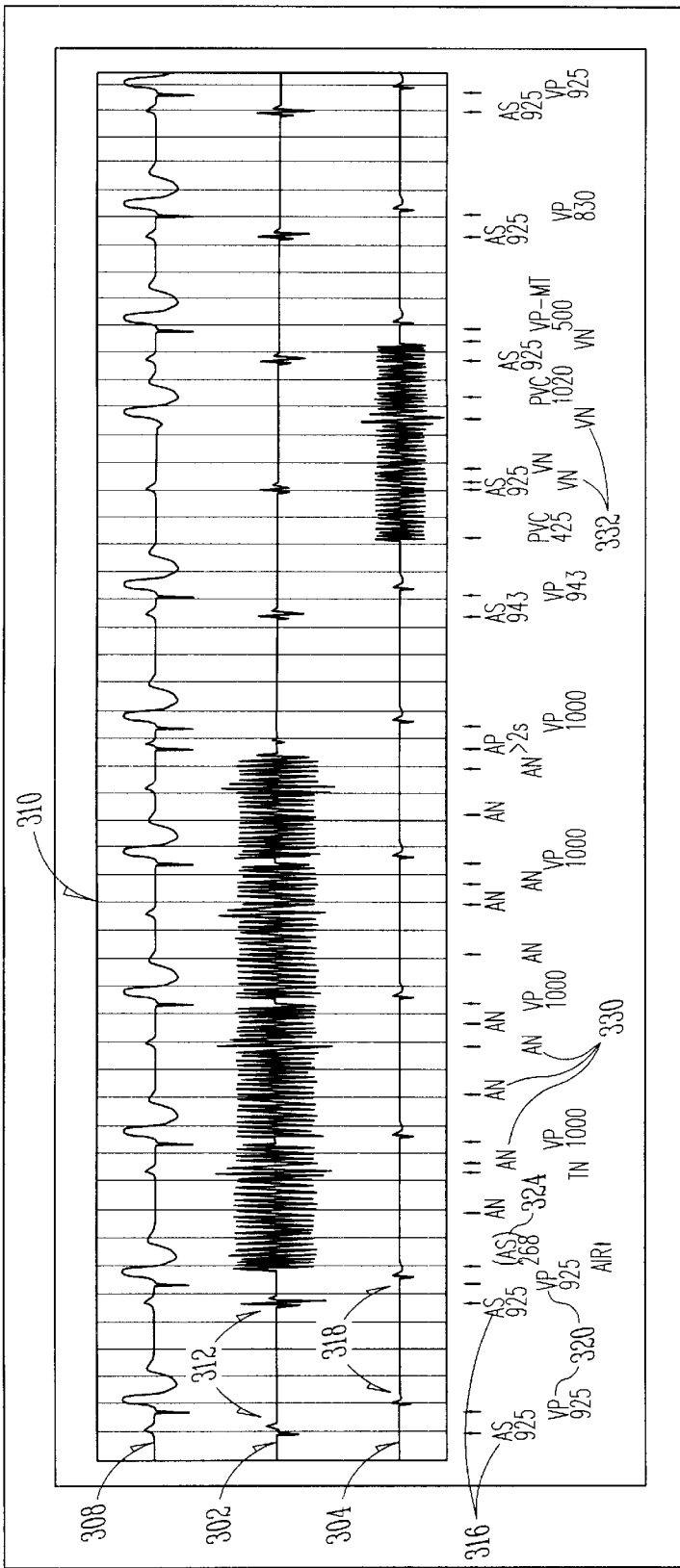
FIG. 3 is one or more cardiac signals and markers according to one embodiment of the present subject matter.

Referring now to FIG. 3, there is shown one embodiment of a display of one or more cardiac signals according to the present subject matter. A first cardiac signal sensed using an implantable pulse generator is shown at 302 and a second cardiac signal sensed using the implantable pulse generator is shown at 304. A third cardiac signal is shown at 308 and is sensed using surface leads attached to the skin of the patient. In one embodiment, the one or more cardiac signals shown in FIG. 3 is a image 310 of cardiac signals as would be displayed on a display screen 311 of a medical device programmer in communication with an implantable pulse generator capable of sensing both a ventricular signal across the ventricular region and an atrial signal across the atrial (or supraventricular) region.

In one embodiment, the first cardiac signal 302 is an atrial signal and the second cardiac signal 304 is a ventricular signal. In the atrial signal 302 there are indications of sensed atrial depolarization shown at 312. In one embodiment, these indications of atrial depolarizations are sensed P-waves. When an atrial depolarization is sensed and identified, the cardiac depolarization marker is generated as previously discussed. After the cardiac depolarization marker is generated it is transmitted to the medical device programmer where it is displayed on the plot 310. In one embodiment, the cardiac depolarization marker for a sensed atrial event is an "AS" (atrial sense event), as is shown at 316.

In the ventricle signal 304 there are indications of sensed ventricular depolarization shown at 318. In the present embodiment, the ventricular depolarizations are initiated by a pacing pulse delivered to the ventricular region. When pacing pulses are delivered to initiate a cardiac depolarization in either the atria or the ventricles, the cardiac depolarization marker is either as a "VP"(ventricular pace) or an "AP" (atrial pace) event. When the depolarization of the region of the heart is sensed (i.e., the depolarization was the result of a naturally occurring depolarization wave) the cardiac depolarization marker is either a "VS"(ventricular sense) or an "AS" (atrial sense) event. In one embodiment, sensed ventricular events include sensed R-waves and/or a QRS-complexes.

When an ventricular depolarization is sensed and identified, the cardiac depolarization marker is generated as previously discussed. After the cardiac depolarization marker is generated it is transmitted to the medical device programmer where it is displayed on the plot 310. In one embodiment, the cardiac depolarization marker for a paced ventricular event is an "VP", as is shown at 320.

The refractory periods start after a sensed or a paced cardiac event. As previously discussed, the present subject matter includes a noise window interval during each refractory period. In one embodiment, the noise window interval occurs during a last portion of the refractory period. In one embodiment, refractory periods have different values depending on whether the cardiac event was sensed or paced. For example, a refractory period for a sensed event, such as a "VS" or "AS" event, the value is programmed to be 135 milliseconds. However, for a paced event, such as a "VP" or "AP" event, the refractory period is a programmable value in the range of 150 milliseconds to 500 milliseconds.

In one embodiment, the last 40 milliseconds of the refractory period is designated as the noise window interval. So, for a sensed event, such as a "VS" event, the refractory period is 135 milliseconds, where the time interval between 95 milliseconds and 135 milliseconds of the refractory period is the noise window. During this interval, the cardiac signals are not ignored, but are analyzed for the presence of noise.

During the noise window interval, a noise event, such as a cardiac complex, is noted on the display screen of the medical device programmer. In one embodiment, if a ventricular complex is sensed during the noise window the first noise marker is generated and transmitted to the medical device programmer. In one embodiment, the first noise marker is a "(VS)" or an "(AS)" and the marker is displayed on the display screen and associated with the approximate location where the sensed complex occurred along the cardiac signal. For a ventricular signal, the display of a "(VS)" marker on the display screen would indicate either noise in the ventricular signal or a long QRS-complex. For an atrial signal, the display of a "(AS)" marker on the display screen would indicate noise in the atrial signal.

In FIG. 3, there is shown an example of a first noise marker. At 324 there is shown a "(AS)" marker indicating that noise occurred during the initial noise window interval in the refractory period. As noise occurred in the initial noise window interval, a subsequent noise window interval is started at the end of the initial noise window interval. Subsequent noise window intervals are repeated as long as noise is sensed during the noise window interval. If noise is sensed in the noise window intervals for the duration of the predetermined time interval the second noise marker is generated and transmitted to the medical device programmer. In one embodiment, the second noise marker is either a "VN" (ventricular noise) or an "AN" (atrial noise). An example of the "AN" is shown at 330 and an example of the "VN" is shown at 332.

In one embodiment, the "AN" and "VN" markers are displayed at no greater than 340 millisecond intervals while there is noise present in the cardiac channel. As FIG. 3 indicates, the "AN" and "VN" markers are plotted consecutively every 340 milliseconds during the time when noise is retriggering the noise window intervals. When noise no longer retriggers the noise window interval, the implantable pulse generator returns to sensing the cardiac signals (e.g., 302 and 304) for the occurrence of either a sensed ("VS" and/or "AS") or a paced ("VP" and/or "AP") cardiac depolarization.

In addition to displaying the one or more cardiac signals, cardiac depolarization markers, first noise markers and second noise markers on a display screen of a medical device programmer, it is also possible to print on paper the at least one cardiac signal, the cardiac depolarization marker, the first noise marker and the second noise marker. For example, the cardiac signals and the markers of the present subject matter can be printed on a strip produced by an ECG chart recorder.

Figure 4:
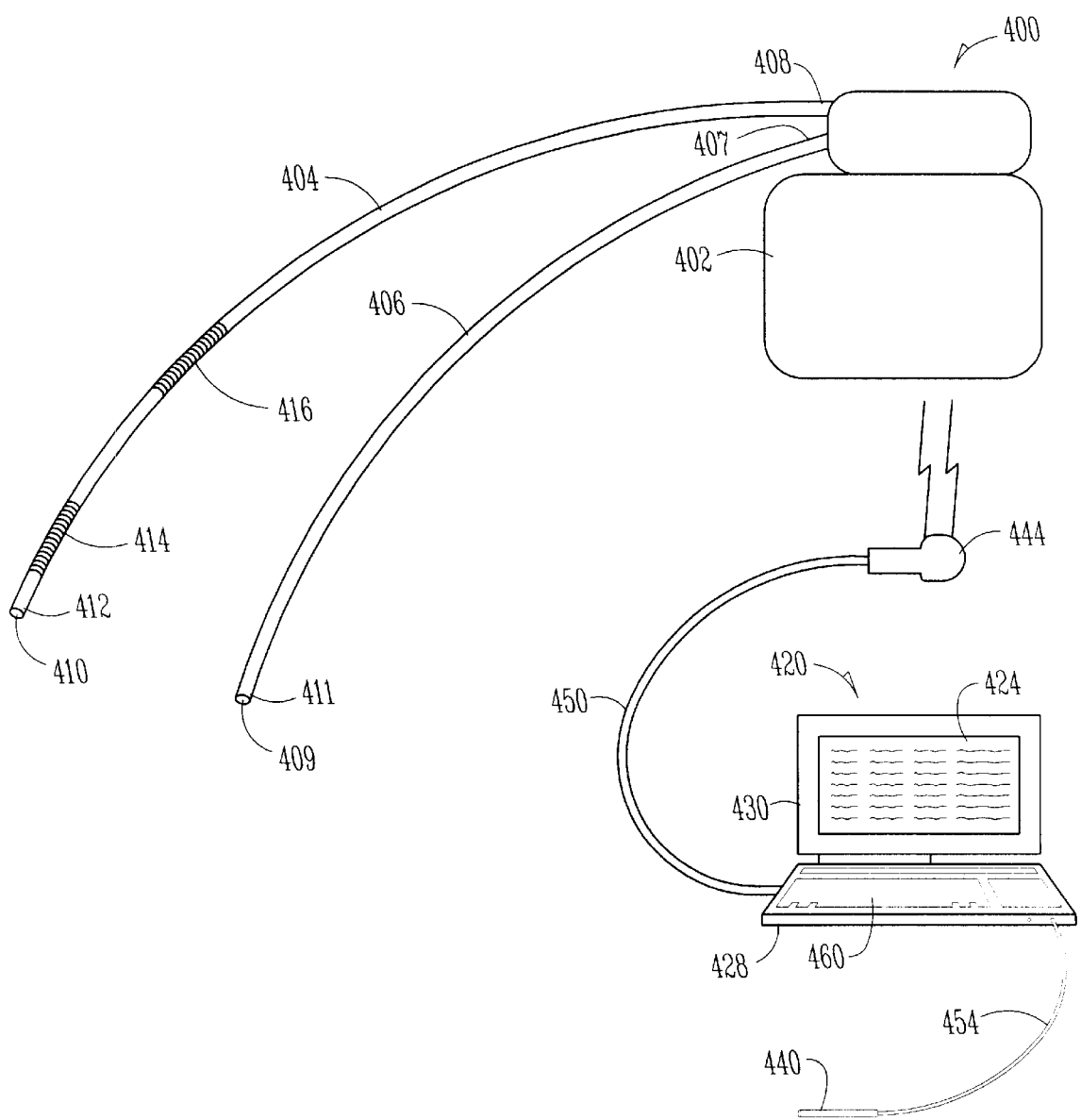
FIG. 4 is a schematic view of an implantable pulse generator and a medical device programmer according to one embodiment of the present subject matter.

Referring now to FIG. 4 there is shown one embodiment of a system according to the present subject matter. The system includes an implantable pulse generator 400. In the present embodiment, the implantable pulse generator 400 is an implantable cardiac defibrillator 402 electrically and physically coupled to at least one intracardiac catheter. In one embodiment, the implantable cardiac defibrillator 402 includes a first intracardiac catheter 404 and a second intracardiac catheter 406, where each of the first and second intracardiac catheters 404 and 406 includes one or more pacing electrodes and the first intracardiac catheter 404 also includes one or more defibrillation electrodes.

The first intracardiac catheter 404 and the second intracardiac catheter 406 are used to sense one or more cardiac signals which contain cardiac complexes each indicative of at least a portion of a cardiac cycle. Electronic circuitry contained within the implantable cardiac defibrillator 402 is used to analyze the sensed cardiac signals and the sensed complexes to determine the occurrence of an arrhythmic episode. Based on the analysis of the cardiac complexes in the cardiac signals, the electronic circuitry within the implantable cardiac defibrillator 402 delivers one or more electrical pulses to electrodes to the first intracardiac catheter 404 and the second intracardiac catheter 406 under certain predetermined conditions to treat the arrhythmic episode.

In one embodiment, the first intracardiac catheter 404 is an endocardial lead that is releasably attached to the cardiac defibrillator 402. The first intracardiac catheter 404 has an elongate body with a proximal end 408 and a distal end 410 and is shown as having a pacing electrode 412 located at, or adjacent, the distal end 410 of the first intracardiac catheter 404. In one embodiment, the pacing electrode 412 is a tip electrode positioned at the distal end 410 of the intracardiac catheter 404. Alternatively, the pacing electrode 412 is an annular, or a semi-annular ring electrode positioned adjacent the distal end 410.

The first intracardiac catheter 404 also includes one or more defibrillation electrodes. In one embodiment, the first intracardiac catheter 404 has a first defibrillation electrode 414 and a second defibrillation electrode 416, where the first defibrillation electrode 414 and the second defibrillation electrode 416 are defibrillation coil electrodes as are known in the art. The first defibrillation electrode 414 is spaced apart and proximal from the pacing electrode 412, and the second defibrillation electrode 416 is spaced apart and proximal from the first defibrillation electrode 414.

In one embodiment, the second intracardiac catheter 406 is an endocardial lead that is releasably attached to the cardiac defibrillator 402. The second intracardiac catheter 406 has an elongate body with a proximal end 407 and a distal end 409 and is shown as having a pacing electrode 411 located at, or adjacent, the distal end 409 of the second intracardiac catheter 406. In one embodiment, the pacing electrode 411 is a tip electrode positioned at the distal end 409 of the second intracardiac catheter 406. Additional pacing/sensing electrodes can also be added along the second intracardiac catheter 406 to allow for bipolar sensing and pacing.

Figure 5:
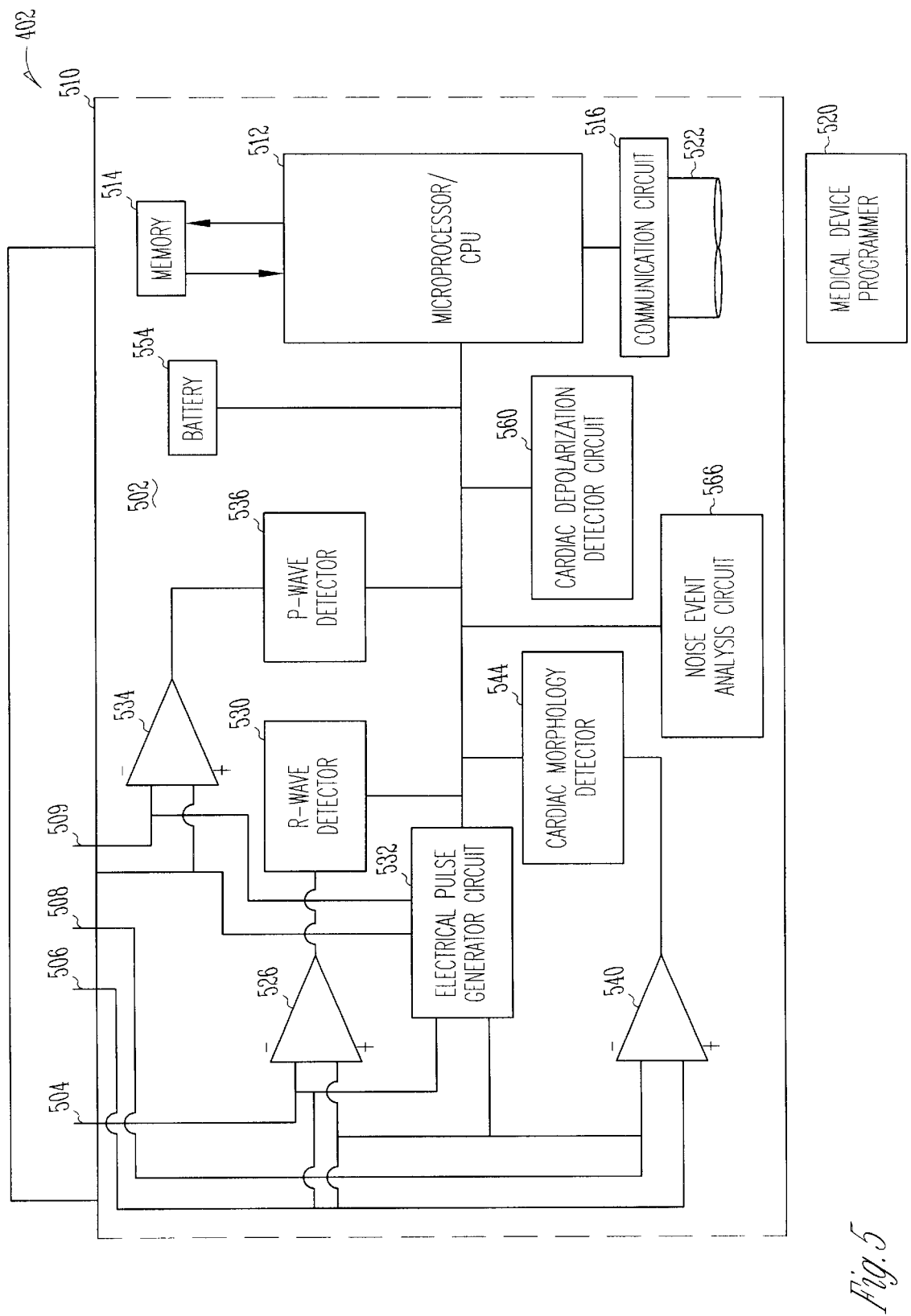
FIG. 5 is a block diagram of an implantable pulse generator according to one embodiment of the present subject matter.

Referring now to FIG. 5, there is shown an embodiment of a block diagram of the implantable cardiac defibrillator 402. The implantable cardiac defibrillator 402 includes control circuitry 502 that couples to the two or more electrodes for receiving at least one cardiac signal that includes indications of cardiac depolarizations and delivering electrical energy to the two or more electrodes. The control circuitry 502 includes terminals, labeled with reference numbers 504, 506, 508 and 509 for connection to electrodes attached to the surface of the first intracardiac catheter 404 and the second intracardiac catheter 406.

The pacing electrode 412 of the first intracardiac catheter 404 is electrically connected to terminal 504 and to the control circuitry 502 through an electrically insulated conductor provided within the elongate body of the first intracardiac catheter 404. The first defibrillation electrode 414 and the second defibrillation electrode 416 are connected to terminals 506 and 508, respectively, and to the control circuitry 502 through electrically insulated conductors provided within the elongate body of the first intracardiac catheter 404. The pacing electrode 411 of the second intracardiac catheter 406 is electrically connected to terminal 509 and to the control circuitry 502 through an electrically insulated conductor provided within the elongate body of the second intracardiac catheter 406.

In one embodiment, the control circuitry 502 of the cardiac defibrillator 402 is encased and hermetically sealed in a housing 510 suitable for implanting in a human body. In one embodiment, titanium is used for the housing 510, however, other biocompatible housing material as are own in the art may be used. A connector block is additionally attached to the housing 510 of the cardiac defibrillator 402 to allow for the physical and the electrical attachment of the first second intracardiac catheters 404 and 406 and the electrodes to the cardiac defibrillator 402 and the encased control circuitry 502.

The control circuitry 502 of the cardiac defibrillator 402 is a programmable rnicroprocessor-based system, with a microprocessor 512 and a memory circuit 514, which contains parameters for various pacing and sensing modes and stores data indicative of cardiac signals received by the control circuitry 502. In one embodiment, the microprocessor times the refractory period and the noise window interval contained within the refractory period through the use of a clock integrated into the control circuitry 502. In one embodiment, the memory circuit 514 stores one or more executable programs used by the implantable cardiac defibrillator 402 to analyze and treat detected arrhythmic episodes. Additionally, the memory circuit 514 stores one or more programs directed to implementing and performing the present subject matter.

A communication circuit 516 is additionally coupled to the control circuitry 502, the memory circuit 514 and the microprocessor 512 to allow the cardiac defibrillator 402 to establish a communication link between the cardiac defibrillator 402 and a medical device programmer 520. In one embodiment, the communication circuit 516 and the medical device programmer 520 use a wire loop antenna 522 and a radio frequency telemetric link, as is known in the art, to receive and transmit signals and data to and from the medical device programmer 520 and the control circuitry 502. In this manner, the one or more cardiac signals, cardiac depolarization markers, first noise markers and second noise markers are transmitted under the control of the microprocessor 512 from the communication circuit 516 to and received by the medical device programmer 520.

The embodiment of the cardiac defibrillator block diagram shows the pacing electrode 404 and the first defibrillation electrode 414 coupled to a sense amplifier 526 to allow for bipolar sensing and pacing. The output of the sense amplifier 526 is connected to an R-wave detector 530. These components serve to sense and amplify R-waves, and apply signals indicative thereof to the microprocessor 512. Among other things, microprocessor 512 responds to the R-wave detector 530 by providing pacing signals to an electrical pulse generator circuit 532 coupled to the microprocessor 512, as needed according to the programmed pacing mode. In one embodiment, the electrical pulse generator circuit 532 provides pacing level pulses to terminals 504 and 506, which connect to the pacing electrode 404 and the first defibrillation electrode 414, for cardiac pacing. Power to the cardiac defibrillator 302 is supplied by an electrochemical battery 554 that is housed within the cardiac defibrillator 402.

The first defibrillation electrode 404 and the second defibrillation electrode 406 are coupled to a sense amplifier 540, whose output is connected to a cardiac morphology detector 544. These components serve to sense and amplify QRS-complexes, and apply signals indicative thereof to the microprocessor 512. In one embodiment, the cardiac morphology detector 544 includes an analog filter for filtering cardiac signal noise sensed by the electrodes. The cardiac signals are then bandlimited before arriving at an analog-to-digital filter. The cardiac signals are then A/D converted into a digital signal and subsequently received by the microprocessor 512. The microprocessor 512 responds to the sensed cardiac signals by providing electrical energy pulses (cardioversion and/or defibrillation pulses) from the electrical pulse generator circuit 532.

The pacing electrode 411 and the housing 510 are coupled to a sense amplifier 534 to allow for unipolar sensing and pacing. The output of the sense amplifier 534 is connected to a P-wave detector 536. These components serve to sense and amplify P-waves, and apply signals indicative thereof to the microprocessor 512. Among other things, microprocessor 512 responds to the P-wave detector 536 by providing pacing signals to an electrical pulse generator circuit 532 coupled to the microprocessor 512, as needed according to the programmed pacing mode. In one embodiment, the electrical pulse generator circuit 532 provides pacing level pulses to terminals 509 and 510, which connect to the pacing electrode 411 and the housing for cardiac pacing.

The control circuitry 502 further includes a cardiac depolarization detector circuit 560 coupled to the microprocessor 512. The cardiac depolarization detector circuit 560 detects the occurrence of cardiac depolarizations in the at least one cardiac signal. As previously discussed, the cardiac depolarizations detected by circuit 560 can include both sensed and paced depolarizations. Upon detecting a cardiac depolarization in circuit 560 the microprocessor 512 starts the refractory period.

A noise event analysis circuit 566 is also coupled to the microprocessor and the cardiac depolarization detector circuit 560. The noise event analyzing circuit 566 analyzes the at least one cardiac signal for noise events during the refractory period. When a noise event is detected by the noise event analysis circuit 566 during the noise window interval, the microprocessor 512 repeats the noise window interval.

The control circuitry 502 generates the cardiac depolarization marker when the cardiac depolarization is identified. In one embodiment, the microprocessor 512 controls the communication circuit 516 to transmit the cardiac depolarization marker when the cardiac depolarization is identified by the cardiac depolarization detector circuit 560. The control circuitry 502 also generates the first noise marker and the second noise marker when noise is detected in the one or more cardiac signals. In one embodiment, the microprocessor 512 controls the communication circuit 516 to transmit the first noise marker when noise events are detected by the noise event analysis circuit 566 during the noise interval window. In one embodiment, the microprocessor 512 controls the communication circuit 516 to transmit the second noise marker when the microprocessor 512 repeats the noise window interval for the predetermined time interval, where the predetermined time interval is time by the microprocessor 512.

Referring again to FIG. 4, there is shown one embodiment of a medical device programmer 420. As previously mentioned, one embodiment of the medical device programmer 420 for the implantable cardiac defibrillator 402 takes the form of an external controller as are known in the art. The medical device programmer 420 is designed to communicate with an implantable medical device, such as the cardiac defibrillator 402, via radio frequency telemetry. The medical device programmer 420 has programmer circuitry, including a microprocessing unit and related circuitry, such as digital memory, which is coupled to a graphics display screen 424.

In one embodiment, the medical device programmer 420 comprises an outer housing 428 which is made of a thermal plastic or other suitable lightweight durable material. The graphics display screen 424 is disposed on the upper surface of housing 430. The graphics display screen 424 folds down into a closed position when medical device programmer 420 is not in use, thereby reducing the size of medical device programmer 420 and protecting the display surface of graphics display screen 424 during transportation and storage.

In an additional embodiment, the external programmer additionally has a floppy disk drive and/or a removable disk drive and a hard drive disposed within the housing. Air vents are provided at various points in the housing so that an internal fan can circulate air within the housing 428 and prevent overheating of components therein.

The medical device programmer 420 is shown with the graphics display screen 424 positioned in one of a plurality of possible open positions such that a display on the graphics display screen 424 is visible to a user situated in front of the medical device programmer 420. In one embodiment, the graphics display screen 424 is of the LCD or electroluminescent type. The graphics display screen 424 is operatively coupled to the electronic circuitry disposed with the housing 428 and is adapted to provide a visual display of graphics and/or data under control of the programmer electronic circuitry.

The medical device programmer 420 further includes a user input device coupled to the electronic circuitry. In one embodiment, the user input device is the graphics display screen 428, which is provided with touch-sensitive capability, such that a user can interact with the programmer electronic circuitry by touching the display area on the graphics display screen 428 with a stylus 440, or even the user's finger. In one embodiment, the touch-sensitive graphics display screen is primary input for the medical device programmer 420.

The medical device programmer 420 further includes a programming head 444, which is place over a patient's body near the implant site of an implanted device, such as the cardiac defibrillator 402, in order to establish a communication link with the communication circuit of the cardiac defibrillator 402. The telemetry link between the cardiac defibrillator 402 and the medical device programmer 420 allows the electronic circuitry coupled to the graphics display screen to be coupled to the control circuitry of the cardiac defibrillator 402. The programming head 444 is coupled to the electronic circuitry of medical device programmer 420 and a receiver circuit for receiving signals from the communication circuit indicative of cardiac signals by a cable 450.

The stylus 440 used to interact with the touch-sensitive graphics display screen 424 is coupled to the programmer electronic circuitry within the housing 428 by a cable 454. Alternatively, the medical device programmer 420 may be equipped with a conventional computer "mouse"-type pointing device or a track-ball, rather than a stylus. In the absence of either a stylus or a mouse, on-screen cursor control for enabling user interaction with medical device programmer 420 may be facilitated through cursor control keys 460 (arrow keys or the like) disposed on the medical device programmer 420.

The medical device programmer 420 further includes a receiver circuit for receiving signals transmitted from the communication circuit, where the signals are indicative of cardiac signals and markers as previously discussed. Through the telemetric contact with the cardiac defibrillator 402, the medical device programmer 420 is capable of capturing and displaying cardiac signals and event markers as previously discussed as they are sensed and detected by the implantable pulse generator. In one embodiment, this occurs in "real time" to allow the operator to realize the implantable pulse generator is operating in an environment where there is ambient noise sufficiently strong to interfere with the sensing and recording of cardiac signals. This information is then transmitted from the cardiac defibrillator 402 and displayed on the graphics display screen 424.

This application is intended to cover any adaptations or variations of the present invention. It is manifestly intended that this invention be limited only by the claims and equivalents thereof.

We claim:

1. A method, comprising:
   sensing at least one cardiac signal with an implantable pulse generator;
   identifying the occurrence of a cardiac depolarization in the at least one cardiac signal and generating a cardiac depolarization marker when the cardiac depolarization is identified;
   analyzing the at least one cardiac signal for a noise event during a refractory period, where the refractory period occurs after the detected cardiac depolarization and where the refractory period includes a noise window interval; and
   repeating the noise window interval when the noise event occurs during the noise window interval.

2. The method of claim 1, where analyzing the at least one cardiac signal includes generating a first noise marker when the noise event occurs during the noise interval window.

3. The method of claim 2, including generating a second noise marker when the noise window interval is repeated for a predetermined time interval.

4. The method of claim 3, including programming the predetermined time interval to a value of 340 milliseconds and the noise window in the refractory period to a duration of forty (40) milliseconds.

5. The method of claim 3, including establishing a communication link between the implantable pulse generator and a medical device programmer, where the medical device programmer includes a display screen;
   transmitting the at least one cardiac signal, which includes the cardiac depolarization, to the medical device programmer; and
   displaying the at least one cardiac signal on the display screen.

6. The method of claim 5, including transmitting the cardiac depolarization marker to the medical device programmer; and
   displaying the cardiac depolarization marker on the display screen with the cardiac depolarization in the at least one cardiac signal.

7. The method of claim 6, including transmitting the first noise marker to the medical device programmer;
   displaying the first noise marker on the display screen; and
   associating the first noise marker and the noise event of the at least one cardiac signal.

8. The method of claim 7, including transmitting the second noise marker to the medical device programmer;
   displaying the second noise marker on the display screen; and
   associating the second noise marker and the at least one cardiac signal at the predetermined time interval.

9. The method of claim 8, including printing on paper the at least one cardiac signal, the cardiac depolarization marker, the first noise marker and the second noise marker.

10. The method of claim 1, where the cardiac signal includes a voltage and analyzing the at least one cardiac signal for the noise event includes detecting when the voltage of the cardiac signal exceeds a predetermined sensing floor value.

11. The method of claim 1, where identifying the occurrence of the cardiac depolarization includes producing a pacing level pulse, and identifying the cardiac depolarization when the pacing level pulse is produced.

12. A system, comprising:
    at least one cardiac lead that includes two or more electrodes;
    control circuitry coupled to the two or more electrodes, where the control circuitry receives at least one cardiac signal that includes indications of cardiac depolarizations and generates a cardiac depolarization marker when the cardiac depolarization is identified, and where the control circuitry includes:
    a microprocessor, where the microprocessor times a refractory period and a noise window interval contained within the refractory period;
    a cardiac depolarization detector circuit coupled to the microprocessor, where the cardiac depolarization detector circuit detects the occurrence of a cardiac depolarization in the at least one cardiac signal and the microprocessor starts the refractory period after the cardiac depolarization; and
    a noise event analysis circuit coupled to the microprocessor and the cardiac depolarization detector circuit, where noise event analyzing circuit analyzes the at least one cardiac signal for noise events during the refractory period, and where the microprocessor repeats the noise window interval when the noise event analysis circuit detects a noise event during the noise window interval.

13. The system of claim 12, where the control circuitry generates a first noise marker when the noise event analysis circuit detects noise events in the noise interval window.

14. The system of claim 13, where the control circuitry generates a second noise marker when the microprocessor repeats the noise window interval for a predetermined time interval.

15. The system of claim 14, where the predetermined time interval is programmed to a value of 340 milliseconds and the noise window in the refractory period is programmed to a duration of forty (40) milliseconds.

16. The system of claim 14, including a communication circuit coupled to the microprocessor; and a medical device programmer, where the medical device programmer includes programmer circuitry and a display screen coupled to the programmer circuitry, and where the medical device programmer establishes a communication link with the communication circuit and the communication circuit transmits the at least one cardiac signal, including the occurrence of the cardiac depolarization, to the programmer circuitry for display on the display screen.

17. The system of claim 16, where the communication circuit transmits the cardiac depolarization marker to the programmer circuitry for display on the display screen.

18. The system of claim 16, where the communication circuit transmits the first noise marker to the programmer circuitry for display on the display screen.

19. The system of claim 18, where the communication circuit transmits the second noise marker to the programmer circuitry for display on the display screen.

20. The system of claim 13, where the at least one cardiac signal includes a voltage, and the noise event analysis circuit detects the noise event when the voltage of the cardiac signal exceeds a predetermined sensing floor value.

21. The system of claim 20, where the predetermined sensing floor value is a programmable value in the range of 0.18 to 0.45 millivolts.

* * * * *